United States Patent [19]
Fulton et al.

[11] 4,453,423
[45] Jun. 12, 1984

[54] METHOD AND APPARATUS FOR GENERATING A NATURAL CRACK

[75] Inventors: Fred J. Fulton, Livermore; Charles A. Honodel, Tracy; William R. Holman, Danville; Richard C. Weingart, Livermore, all of Calif.

[73] Assignee: The United States of America as represented by the United States Department of Energy, Washington, D.C.

[21] Appl. No.: 375,645

[22] Filed: May 6, 1982

[51] Int. Cl.³ ............................................. G01N 1/28
[52] U.S. Cl. ................................... 73/863; 29/421 E; 73/799
[58] Field of Search .................... 73/783, 799, 863; 29/421 E; 102/701, 202.7; 225/1

[56] References Cited

U.S. PATENT DOCUMENTS

| | | |
|---|---|---|
| 2,703,297 | 3/1955 | MacLeod .......................... 29/421 E |
| 3,076,408 | 2/1963 | Poulter . |
| 3,353,401 | 11/1967 | Hessler . |
| 3,376,633 | 4/1968 | Wesley .................................. 29/421 |
| 3,482,437 | 12/1969 | Martens . |
| 3,669,022 | 6/1972 | Dahn .................................. 102/202.7 |
| 3,680,367 | 8/1972 | Krafft . |
| 4,075,884 | 2/1978 | Barker . |
| 4,090,489 | 5/1978 | Barker . |

Primary Examiner—S. Clement Swisher
Attorney, Agent, or Firm—Paul Davis; Harold M. Dixon; Michael F. Esposito

[57] ABSTRACT

A method and apparatus for generating a measurable natural crack includes forming a primary notch in the surface of a solid material. A non-sustained single pressure pulse is then generated in the vicinity of the primary notch, resulting in the formation of a shock wave which travels through the material. The shock wave creates a measurable natural crack within the material which extends from the primary notch. The natural crack formed possesses predictable geometry, location and orientation.

16 Claims, 9 Drawing Figures

METHOD AND APPARATUS FOR GENERATING A NATURAL CRACK

FIELD OF THE INVENTION

The U.S. Government has rights in this invention pursuant to Contract W-7405-ENG-48 between the U.S. Department of Energy and the University of California for the operation of Lawrence Livermore National Laboratory.

BACKGROUND OF THE INVENTION

The present invention relates generally to a method and apparatus for studying fracture behavior of materials and structures, and more particularly a method and apparatus for generating a measurable natural crack having predictable geometry, location and orientation into a solid material.

Fracture behavior studies of materials and structures include determinations and/or measurements of fracture toughness; structural tests with controlled defects simulating natural defects in structures including, but not limited to, critical shipping containers, aircraft parts, and ship structures; moving cracks in prestressed structures or materials; and crack arrest behavior of materials and structures, e.g., investigating the conditions under which a moving crack will stop.

Prior to the 1940's, fracture safe design procedures for materials were essentially nonexistent. It wasn't until catastrophic failures of many of the World War II "Liberty Ships" occurred that the problem of improved fracture characteristics of metals was finally brought to attention. Fracture initiation in even a minute element of the structure could result in nearly instantaneous fracture of the ship's hull. To this day, the study of fracture initiation and fracture toughness of a material or structure is vital for design criteria.

Fracture resistance or fracture toughness is the inherent resistance of a material to propagation of a pre-existing crack. It is a mechanical property which is very sensitive to the composition, microstructure and prior thermomechanical treatment of the material. All engineering structures have defects (pre-existing cracks) at which fracture will initiate when the stress intensity at the crack tip exceeds a *critical* value. The stress intensity at the crack tip is determined by the loading on the structure (stress) and the crack size, but the *critical* value (the stress intensity above which the crack will enlarge at a catastrophic rate) is independent of the engineering design or the loading—i.e., it is a property of the material itself. Therefore, to prevent fracture, the stress intensity must be kept below the critical level, and it is equally important that (1) the stresses are within specified limits, (2) the defects are within tolerable sizes, and (3) the material has adequate fracture toughness ($K_{IC}$).

The standard ASTM method for evaluating plane strain fracture toughness generally requires preliminary insertion of low stress fatigue cracks in a notch formed in the material specimen. With early efforts to characterize better fracture, cracks were simulated with sharply-tipped notches. No matter how sharp the notch was machined, however, a natural fatigue crack would often result in still lower values of the fracture toughness. Because pre-existing cracks rather than notches are the usual source of difficulty with engineering structures, the fatigue crack was specified as mandatory for valid tests of fracture toughness $K_{IC}$ (e.g., see ASTM test method E-399).

Conventional methods of cracking are very slow and costly, and are designed typically for one specimen at a time. Consider the growth rate of 2 micro-inches per cycle. Approximately 50,000 cycles are required for 1/10" of crack growth, typically 25 minutes at 2,000/minute. At these rates, it is not unusual to average about 60 minutes per specimen when allowance for set-up time, crack initiation from the notch, and shut-down for intermittent examinations are considered. Additionally, high capital equipment costs of this method are undesirable.

An apparatus for measuring fracture toughness of a specimen material is disclosed in U.S. Pat. No. 4,075,884, dated Feb. 28, 1978, to Barker. The fracture specimen loading machine apparatus includes a load-generating portion at a pressure bag adapted to be disposed within a flawed portion of the specimen material. Hydraulic fluid is introduced into the pressure bag, causing an expansion which effectively loads the specimen. A pressure sensor is included for measuring the hydraulic fluid pressure within the pressure bag. The hydraulic fluid creates either a sustained pressure within the notch of the specimen, or alternatively is applied in cyclic form. In either case, a natural crack is not formed; rather, the specimen undergoes plastic deformation in the vicinity of the crack tip, and the material's fracture toughness is altered.

It is desirable to provide a method and apparatus for studying fracture behavior of materials and structures which is useful to study and/or determine fracture toughness; structural tests with controlled defects simulating natural defects; moving cracks in prestressed materials or structures; and crack arrest behavior in materials and structure. More particuarly, it is desirable to create a measurable natural crack in a structure or material without initiating significant plastic deformation. In other words, it would be desirable to create a natural crack possessing predictable geometry, location and orientation without administering a sustained shock pulse, or a series of cyclic pulses to a solid material or structure.

SUMMARY OF THE INVENTION

Accordingly, an object of the invention is to provide a method and apparatus for studying fracture behavior of solid materials or structures.

Another object of the invention is to provide a method and apparatus for studying fracture behavior of materials and structures including fracture toughness; structural tests with controlled defects simulating natural defects; studying moving cracks in prestressed structures or materials; and determining crack arrest behavior of materials and structures.

Yet another object of the invention is to provide a method and apparatus for studying fracture behavior of materials and structures in a fast and efficient manner.

A further object of the invention is to provide a method and apparatus for studying fracture behavior of materials and structures without administering sustained shock pulses, or a series of cyclic pulses to the material or structure.

Yet another object of the invention is to provide a method and apparatus for generating a natural crack in a solid material or structure, wherein the natural crack possesses predictable geometry, location and orientation.

Still a further object of the invention is to provide a method and apparatus for generating a measurable natural crack in a solid material or structure without causing significant plastic deformation of the material or structure.

Yet another object of the invention is to provide a method and apparatus for generating a measurable natural crack in a solid material or structure without administering a sustained shock pulse, or a series of cyclic pulses to the material or structure.

Additional objects, advantages and novel features of the invention will be set forth in part in the description which follows, and in part will become apparent to those skilled in the art by examination of the following, or may be learned by practice of the invention. The objects and advantages of the invention may be realized and attained by means of the instrumentalities and combinations particularly pointed out in the appended claims.

To achieve the foregoing and other objects, and in accordance with the purpose of the present invention as embodied and broadly described herein, the method for generating a measurable natural crack in a solid material may comprise forming a primary notch in a surface of the solid material. A non-sustained single pressure pulse is thereafter created in the vicinity of the primary notch, and travels in a direction through the primary notch to eventually contact the material. Afterwards, a shock wave is formed within the material, moving in a direction through the material and away from the primary notch. A measurable natural crack is formed within the material which extends from the primary notch, and possesses predictable geometry, location and orientation.

In a further aspect of the present invention, and in accordance with its objects and purposes, the apparatus for generating a measurable natural crack in a material may comprise means for forming a notch in the surface of the specimen. Means for generating a non-sustained single pressure pulse in the vicinity of the notch are included. In a further aspect of the present invention, the means for generating the pressure pulse may include a vaporizable electrically-conductive material. Two electrodes are disposed at opposing ends of the electrically-conductive material. A power source is included, and means for operatively connecting the power source to the electrodes is provided.

The apparatus and method for generating a measurable natural crack of predictable geometry, location and orientation in a solid material, as disclosed herein, is achieved without causing significant plastic deformation in the material. This natural crack is formed without administering a sustained shock pulse or a series of cyclic pulses to the material. Additionally, formation of such a natural crack enables one to study the fracture behavior of a material, more particularly fracture toughness, perform structual tests with controlled defects simulating natural defects, study moving cracks in prestressed structures or materials; and determine crack arrest behavior of materials and structures.

BRIEF DESCRIPTION OF THE DRAWINGS

The accompanying drawings, which are incorporated and form a part of the Specification, illustrate many embodiments of the invention, and, together with the Description, serve to explain the principles of the invention.

FIG. 2a is a cross sectional view of the solid material illustrated in FIG. 2, taken along the lines of 2a—2a.

FIG. 3a is a cross sectional view of the solid material illustrated in FIG. 3, taken along the lines 3a—3a.

FIG. 5 illustrates an electrically conductive ribbon of material disposed within the primary notch illustrated in FIG. 2a.

FIG. 6 illustrates a natural crack formed in the solid material of FIG. 2.

FIG. 6a is a cross sectional view of the solid material and natural crack of FIG. 6, taken along the lines 6a—6a.

DETAILED DESCRIPTION OF THE INVENTION

Figure 1:
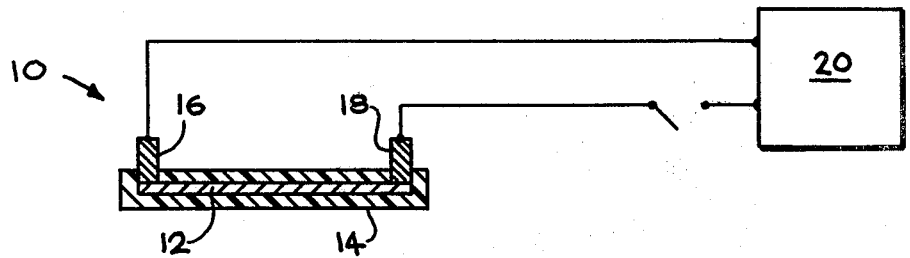
FIG. 1 illustrates schematically one embodiment of an apparatus for generating a non-sustained single pressure pulse.

The method and apparatus of the present invention is directed to the formation of a measurable natural crack within a solid material or structure possessing predictable geometry, location and orientation. This natural crack is formed without causing significant plastic deformation to the material, and achieved without applying a sustained shock pulse or a series of cyclic pulses.

Natural crack is defined herein as a crack which, when examined in cross section, has a tip whose radius is infinitely sharp, i.e., approaching atomic dimensions, and is formed in a manner to minimize plastic deformation in the vicinity of the crack tip. When used in fracture toughness testing, this crack will give the minimum fracture toughness value for a given material.

Fracture behavior of materials and structures can be determined through the generation of such a measurable natural crack. In particular, the measurable natural crack of the present invention may be formed in a solid material or structure to: test for fracture toughness; test structures with controlled defects simulating natural defects including, but not limited to, critical shipping containers, aircraft and ship parts; study moving cracks in prestressed materials or structures; and determine crack arrest behavior of materials and structures, e.g., investigate the conditions under which a moving crack will stop.

Suitable materials for the natural crack include, but are not limited to, metals, alloys, polymers, ceramics, composite materials, and glasses. Exemplary polymers include, but are not limited to, polymethylmethacoylate, polycarbonate, polyvinylchlorine, polystyrene, nylon, and the like. Among the brittle materials are structural steel at low temperature, cast iron, beryllium, tungsten, high temperature alloys, as well as tool, die, and bearing steels and the like. Exemplary ceramics include, but are not limited to, $B_4C$, $Al_2O_3$, $WC$ and the like.

In generating a measurable natural crack having predictable geometry, location and orientation in a solid material, a primary notch is first formed in the material. Thereafter, a non-sustained single pressure pulse is generated in the vicinity of the notch, traveling in a general direction through the primary notch until it contacts the material. Once the pressure pulse has transferred its energy to the material, a shock wave is formed therein. The shock wave moves in a direction away from the primary notch, resulting in the creation of a measurable natural crack within the material. This natural crack extends from the primary notch.

An apparatus for generating a measurable natural crack having predictable geometry, location and orientation in a solid material comprises means for forming a primary notch in the surface of the material, and means for generating a non-sustained single pressure pulse in the vicinity of the primary notch. Such means for forming the primary notch are well known in the art, and are explained in greater detail hereinafter.

Referring now to FIG. 1, one embodiment of an apparatus for generating a single non-sustained pressure pulse is shown generally as 10. A vaporizable electrically conductive ribbon of material 12 is included, as is a layer of insulating material 14 in surrounding relationship to material 12. Exemplary vaporizable materials include metals and alloys which, upon the receipt of a sudden burst of electrical energy, can become vaporized. A preferred conductive material is aluminum. A suitable insulating material is polyester film. Insulator 14 may be applied on conductive material 12 by suitable coating means including, but not limited to, general laminating techniques, adhesive bonding and the like.

A pair of electrodes 16 and 18 is included. Each electrode is disposed at an opposing end of the electrically conductive material 12. The electrodes may be formed from any substance which conducts electricity. The preferred material is copper. A power source 20 is operatively connected to electrodes 16 and 18, respectively. Power source 20 must be a high current source which delivers current to conductive material 12 in a rapid time period sufficient to cause it to vaporize. A capacitor bank is the preferred power source.

Figure 2:
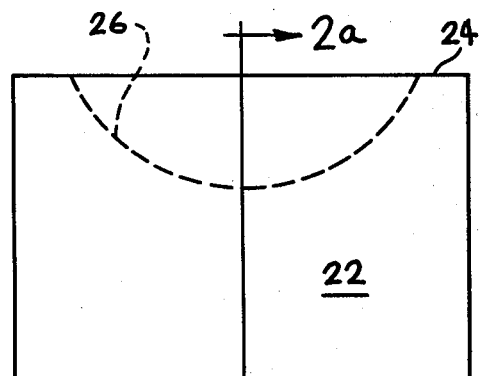
FIG. 2 illustrates a perspective view of a solid material which may be used in conjunction with the formation of the natural crack, including a thumbnail primary notch formed in a surface of the solid material.
Figure 2A:
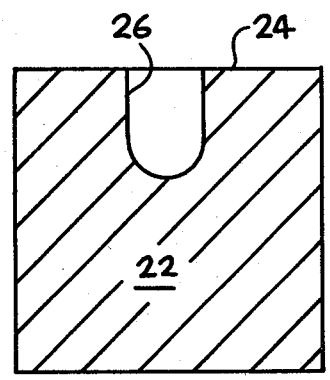

Referring now to FIGS. 2 and 2a, a solid material 22 includes a surface 24 wherein a primary notch 26 is formed. Various methods may be employed to form primary notch 26. However, mechanical means well known in the art are generally employed. Such methods include milling, grinding, electrical discharge machining, and the like. For purposes of the present invention, the geometric configuration of primary notch 26 is immaterial. As shown in FIGS. 2 and 2a, primary notch 26 has a thumbnail configuration. Other configurations are possible.

Figure 3:
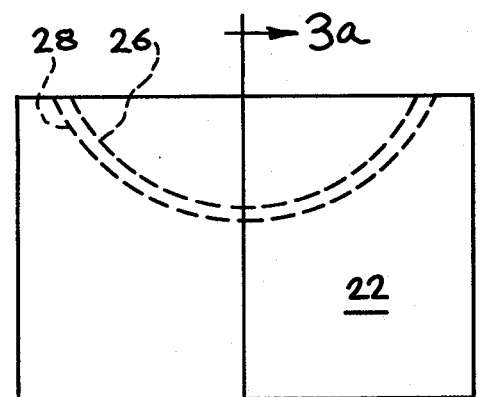
FIG. 3 illustrates a perspective view of a solid material similar to FIG. 2, further illustrating a secondary notch disposed in adjacent relationship to the primary notch of FIG. 2.
Figure 3A:
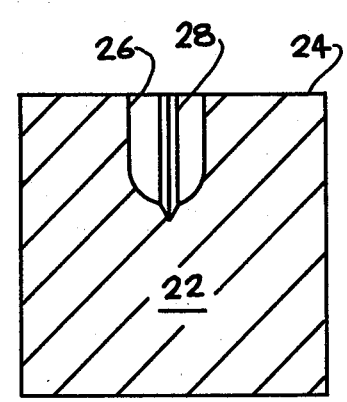

Formation of primary notch 26 extending from surface 24 of the solid material, as shown in FIGS. 2, 2a, 3 and 3a, is necessary in order to direct the pressure pulse into the body of material 22. For certain applications, it may be desirable to include a secondary notch 28 disposed in adjacent relationship to primary notch 26 as illustrated in FIGS. 3 and 3a. It may also be desirable to include a tertiary notch (not shown) positioned adjacent to secondary notch 28. Inclusion of the additional notches serves to more accurately position the natural crack. When a secondary notch is included, the natural crack formed will extend therefrom. The same is true of a tertiary notch. Secondary and tertiary notches can be formed through use of the means recited earlier for forming the primary notch.

Figure 4:
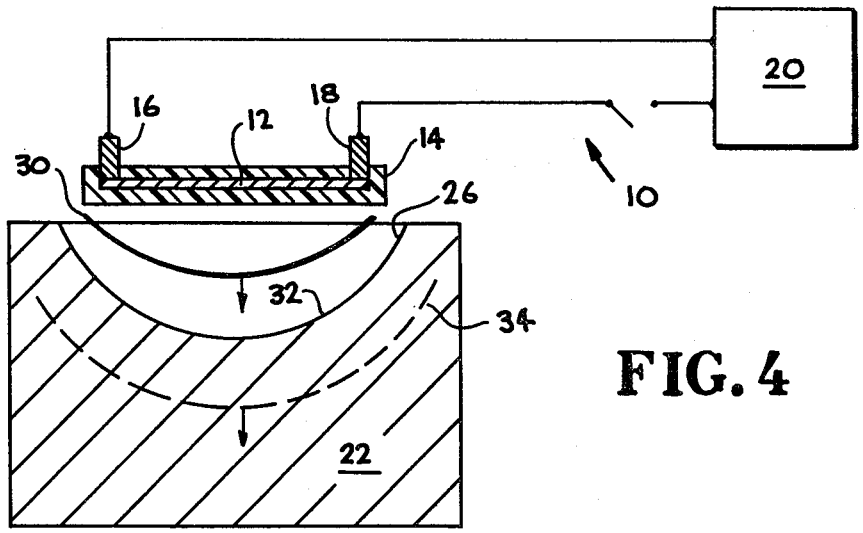
FIG. 4 illustrates schematically the use of the apparatus illustrated in FIG. 1, wherein an electrically conductive ribbon of material is disposed in the vicinity of the primary notch formed in the material.

One embodiment of the method for forming a natural crack in a solid material, wherein an apparatus for generating a non-sustained single pressure pulse (the apparatus being illustrated in FIG. 1), is shown in FIG. 4. In this embodiment, apparatus 10 is disposed in the vicinity of primary notch 26. More specifically, the electrically conductive ribbon of material 12 is disposed adjacent to material 22 and at the exterior of primary notch 26. Power source 20 supplies a sudden burst of electrical energy to conductive material 12. Conductive material 12 is vaporized after it is charged with the electrical energy, creating a non-sustained single pressure pulse 30 in the vicinity of primary notch 26. Pressure pulse 30 travels in a direction through primary notch 26, contacting material 22 at the surface 32 of primary notch 26. When pressure pulse 30 contacts surface 32, a shock wave 34 is formed within material 22, moving in a direction through the material away from primary notch 26.

Figure 5:
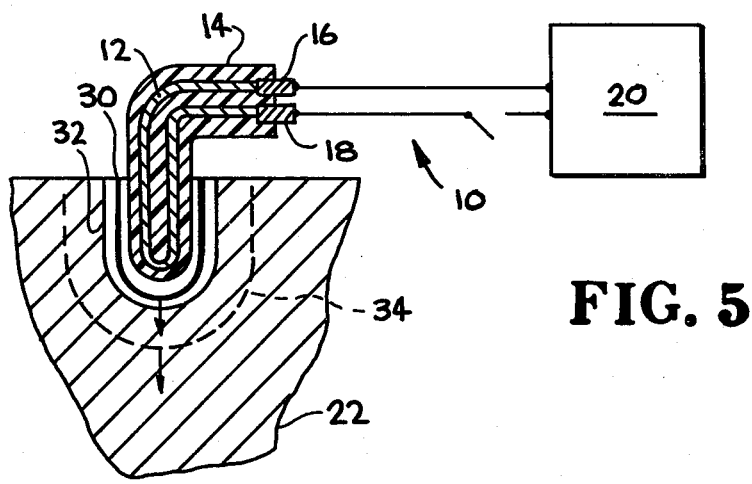

In a second embodiment of the invention, as illustrated in FIG. 5, the electrically conductive ribbon of material 12 (from FIG. 1) is disposed within the interior of primary notch 26, in spaced-apart relationship from material 22. In this embodiment, conductive material 12 forms a loop within primary notch 26 and is spaced-apart from surface 32 by being surrounded by insulating layer 14. Pressure pulse 30 travels a shorter distance than if conductive material 12 is disposed at the exterior of primary notch 26. Less energy is lost with this embodiment. Again, pressure pulse 30 contacts the surface 32 of primary notch 26, and imparts its energy to material 22, resulting in the formation of shock wave 34.

Figures 6, 6A:
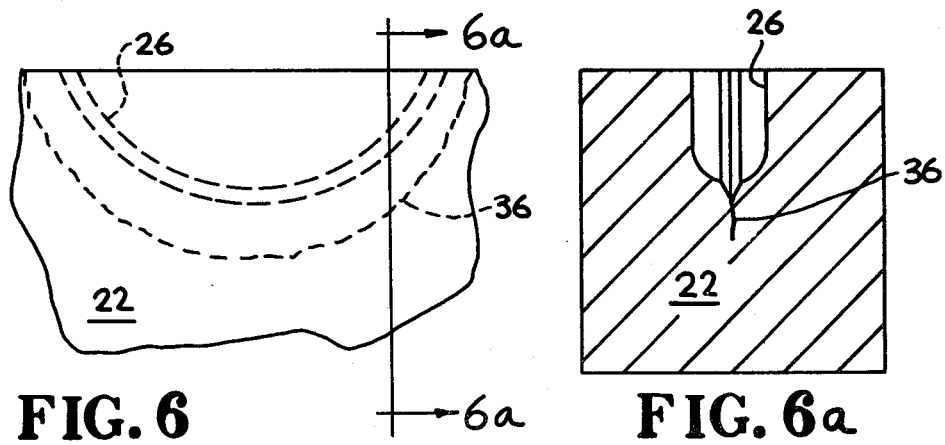

The amount of energy transferred to material 22 is calculated and predetermined so that the natural crack 36 which develops, as shown in FIGS. 6 and 6a, possesses predictable geometry, location and orientation. Crack 36 can initiate at any point along the surface of the primary notch, and if secondary tertiary notches are included, the natural crack formed extends from these notches.

In one embodiment of the invention, the amount of energy delivered by power source 20 is reduced so conductive material 12 is not caused to vaporize. Instead, an electromagnetic induced pulse is created and utilized to generate the pressure pulse. This embodiment of the invention is particularly suitable for materials such as glasses and ceramics which do not require much energy to form the natural crack.

The size of the primary notch, as well as the dimensions of the electrically conductive material utilized to create the non-sustained single pressure pulse, can vary. The two parameters are coordinated in a manner so that the combination results in the formation of a measurable natural crack. Additionally, the kind of solid material employed is a factor which is considered in determining the size of the primary notch and the amount of conductive material. As previously mentioned, ceramics and glasses require less energy to generate a natural crack. Therefore, with these materials a small notch and less electrically conductive material is required.

The following examples are meant to exemplify certain embodiments of the present invention, and are not regarded as limiting its scope which is defined in the appended claims.

EXAMPLES 1 through 4

Natural cracks were generated in a 515 grade 70 steel. Each piece was cut from the same original 8'×20'×1" plate. Chemical analysis indicated a composition as follows: C—0.28; Mn—0.81; Si—0.23; S—0.017; and P—0.012. The heat treatment number designated by the Earle M. Jorgensen Steel Company of Oakland, Calif., was 513060/12-1. Preliminary material properties provided by the Company showed a yield strength of 53.5 ksi, an ultimate tensile strength of 83.4 ksi, with a 22% elongation. A primary notch was formed in each of the test specimens. Disposed within each primary notch was a thin foil of aluminum positioned between two copper electrodes. The copper electrodes were operatively connected to a capacitor bank having the following characteristics: capacitance of 14.7 F; resistance of 0.021; and inductance of 238 nH. Other significant parameters of the capacitor bank were a foil burst time of about 1.7 microseconds; foil burst current of about 70 kA; and foil burst voltage of approximately 7 KV. The bank energy, $\frac{1}{2}CV^2$, was determined to be about 1,440 joules, and the best estimate of foil efficiency estimated at about 10%, yielding approximately 144 joules delivered to the primary notch. A summation of the results of Examples 1–4 is found in Table 1. Nominal cross section is defined as width times thickness of the specimen. Local cross section is defined as the nominal area minus the area of the primary notch (approximately 0.4 in$^2$) Nominal stress is the load divided by the nominal cross section, and local stress is the load divided by the local cross section. In each example, a natural crack was formed which did not breach the integrity of the steel.

EXAMPLE 5

A primary notch is machined in a solid material formed from nylon. An apparatus for generating a pressure pulse includes a capacitor bank operatively connected to a pair of electrodes and a thin foil of aluminum. The foil is disposed within the primary notch, in spaced-apart relationship therefrom. Sufficient energy is discharged from the capacitor bank, causing the vaporization of the aluminum foil and the ultimate formation of a pressure pulse and shock wave within the polymer. The amount of energy supplied to the foil is of sufficient magnitude as to eventually generate a running crack in the test specimen, but not large enough to cause catastrophic failure of the specimen.

EXAMPLE 6

The same procedure as Example 5 is followed. However, tungsten is substituted for the nylon. Sufficient energy is again generated to vaporize the aluminum foil and create a non-sustained single pressure pulse, which later forms a shock wave within the test specimen. The magnitude of the energy delivered to the test specimen is sufficient as to generate a natural crack extending from the primary notch formed in the specimen, but insufficient to cause catastrophic failure.

EXAMPLE 7

The same procedure as Example 5 is followed, except the ceramic material B$_4$C is substituted for the nylon. Energy is discharged from a capacitor bank into a thin foil of aluminum which is disposed in a previously formed primary notch in the ceramic. The amount of energy discharged is carefully controlled so that the foil does not vaporize, but rather generates an electromagnetic pulse. A natural crack having predictable geometry, location and orientation is formed in the ceramic, and extends from the primary notch.

TABLE I

| Example No. | Nominal Cross Section in$^2$ | Local Cross Section in$^2$ | Capacitor Voltage kV | Capacitor Bank Energy $\frac{1}{2}CV^2$ J | Approx. Foil Energy | Nominal Stress ksi | Local Stress ksi |
|---|---|---|---|---|---|---|---|
| 1 | 4.9  | 4.5  | 14 | 1440 | 144 | 35.1 | 38.2 |
| 2 | 5.05 | 4.65 | 14 | 1440 | 144 | 34.7 | 37.6 |
| 3 | 4.9  | 4.5  | 14 | 1440 | 144 | 33.7 | 36.7 |
| 4 | 4.9  | 4.5  | 14 | 1440 | 144 | 36.7 | 40.7 |

We claim:

1. A method for generating a measurable natural crack in a solid material specimen, comprising:
   forming a primary notch in a surface of said solid material;
   creating a non-sustained single pressure pulse in the vicinity of said notch, traveling in a direction through said primary notch and contacting said material;
   forming a shock wave within said material from said pressure pulse, said shock wave moving through said material in a direction away from said primary notch; and
   creating a measurable natural crack within said specimen extending from said primary notch, said natural crack having a predictable geometry, location and orientation within said solid material.

2. The method for generating a measurable natural crack according to claim 1, further comprising forming a secondary notch within said primary notch.

3. The method for generating a measurable natural crack according to claim 1, wherein said single pressure pulse is created by vaporizing an electrically conductive material positioned adjacent and at the exterior of said primary notch.

4. The method for generating a measurable natural crack according to claim 1, wherein a single pressure pulse is created by vaporizing an electrically conductive material within said primary notch in spaced-apart relationship from said solid material.

5. The method for generating a measurable natural crack according to claims 3 or 4, wherein said electrically conducting material is a rIbbon of aluminum.

6. The method for generating a measurable natural crack according to claims 3 or 4, wherein said electrically conductive material is vaporized by receiving a sudden burst of electrical energy from a power source.

7. The method for generating a measurable natural crack according to claim 6, wherein said power source is a capacitor bank operatively connected to said electrically conductive material.

8. The method for generating a measurable natural crack according to claims 3 or 4, wherein said specimen is formed from a material selected from metals, alloys, polymers, ceramics and glasses.

9. The method for generating a measurable natural crack according to claim 4, wherein a layer of insulating material is disposed in surrounding relationship to said electrically conductive material.

10. The method for generating a measurable natural crack according to claim 1, wherein said primary notch has a thumbnail geometric configuration.

11. The method for generating a measurable natural crack according to claim 2, wherein said secondary notch has a thumbnail geometric configuration.

12. An apparatus for generating a measurable natural crack in a solid material, comprising:
- means for forming a primary notch in a surface of said solid material; and
- means for generating a non-sustained single pressure pulse in the vicinity of said primary notch, said means for generating comprising:
- an electrically conductive ribbon of material,
- two electrodes, each disposed at opposing ends of the electrically conductive material,
- a power source, and
- means for operatively connecting said power source to said electrodes.

13. The apparatus for generating a measurable natural crack in a solid material according to claim 13, further comprising a layer of insulating material positioned between said electrodes, in surrounding relationship to said electrically conductive material.

14. The apparatus for generating a measurable natural crack in a solid material according to claim 13, wherein said electrically conductive material is aluminum.

15. The apparatus for generating a measurable natural crack in a solid material according to claim 13, wherein said electrodes are formed of copper.

16. The apparatus for generating a measurable natural crack in a solid material according to claim 13, wherein said power source is a capacitor bank.

* * * * *